United States Patent [19]

Itoi et al.

[11] Patent Number: 5,340,521
[45] Date of Patent: Aug. 23, 1994

[54] MELT VISCOSITY DEPRESSANT FOR POLYESTER RESIN AND POLYESTER RESIN COMPOSITION COMPRISING THE SAME

[75] Inventors: Akito Itoi; Isao Nishi; Yasuo Ishii, all of Wakayama, Japan

[73] Assignee: Kao Corporation, Tokyo, Japan

[21] Appl. No.: 917,378

[22] Filed: Jul. 23, 1992

[30] Foreign Application Priority Data

Jul. 24, 1991 [JP] Japan .................................. 3-184513
Dec. 16, 1991 [JP] Japan .................................. 3-331998
Mar. 4, 1992 [JP] Japan .................................. 4-46880

[51] Int. Cl.$^5$ .................... B27C 47/00; C08F 20/00
[52] U.S. Cl. ................... 264/176.1; 528/293; 528/295; 528/296; 528/298; 528/300; 528/302; 528/304; 528/307; 528/308; 528/308.6; 528/373; 525/437; 428/364
[58] Field of Search .............. 528/272, 293, 295, 296, 528/298, 300, 302, 304, 307, 308, 308.6, 373; 525/437; 428/364; 264/176.1

[56] References Cited

U.S. PATENT DOCUMENTS 4,273,942 6/1981 Mark et al. ............................ 568/42
4,282,134 8/1981 Mark et al. ........................... 524/170

FOREIGN PATENT DOCUMENTS 0063180 10/1982 European Pat. Off. .
0119554 9/1984 European Pat. Off. .
2832055 1/1980 Fed. Rep. of Germany .

OTHER PUBLICATIONS

CA116(6):43029x.
CA115(6):50412z.
CA99(6):39742n.
CA116(2):7128v.

*Primary Examiner*—John Kight, III
*Assistant Examiner*—Sam A. Acavah
*Attorney, Agent, or Firm*—Oblon, Spivak, McClelland, Maier & Neustadt

[57] ABSTRACT

A new melt viscosity depressant for a polyester resin having a structure of an aromatic carbonyl compound is disclosed.

Addition of the melt viscosity depressant to a polyester resin reduces the melt viscosity of the resin remarkably, thereby facilitating mold processing and melt-spinning of the polyester resin composition, from which high strength polyester molding products and polyester fibers can be obtained.

11 Claims, No Drawings

MELT VISCOSITY DEPRESSANT FOR POLYESTER RESIN AND POLYESTER RESIN COMPOSITION COMPRISING THE SAME

FIELD OF THE INVENTION

The present invention relates to a melt viscosity depressant for a polyester resin, a polyester resin composition comprising said melt viscosity depressant, and a polyester fiber which is obtained by melt-spinning such a polyester resin composition.

BACKGROUND OF THE INVENTION

Polyester resins are widely used as molding products or synthetic fibers. Increasing the strength of a molding product or fiber may be probable by increasing the degree of polymerization of the polymer. However, when the degree of polymerization of the polymer is increased, the melt viscosity thereof is increased as a matter of course impairing the workability thereof and reducing the productivity. Although elevation of the melting temperature is one approach for reducing the melt viscosity, the decomposition of the resin is accelerated to reduce the degree of polymerization of the polymer. Thus, it cannot be achieved to produce a molding product or a fiber having a high degree of polymerization and high strength.

Polyester resins are widely used on account of their various excellent characteristics. However, they have low dyeability and can hardly be dyed except with disperse dyes. Among various proposals to improve the dyeability of polyester resins, copolymerization of an isophthalic acid component containing a sulfonic acid salt moiety enables the polyester to be dyed with cationic dyes, as disclosed e.g. in JP-B-34-10497 (1959) (the term "JP-B" as used herein means an "examined published Japanese patent application").

However, such a polymerization system causes a considerably increased melt viscosity of resin due to the thickening effect of the sulfonate-containing isophthalic acid component, and the resin thus obtained has a low moldability. Therefore, it is difficult to produce a cationic dye-dyeable polyester resin having a high degree of polymerization and high strength.

In order to overcome these problems, the addition of a lubricant has been suggested. For example, the addition of ethylenebisstearamide, stearic acid and stearyl alcohol as a lubricant to a resin compound decreases the melt viscosity, nevertheless the degree of polymerization of the resin also decreases.

On the other hand, aromatic ether compounds, alkyl diphenyl compounds and aromatic imide compounds have been known as a melt viscosity depressant for polyester resin, as disclosed in JP-A-3-223382 (1991) and JP-A-3-223383 (1991) (the term "JP-A" as used herein means an "unexamined published Japanese patent application").

However, as the compatibility of these compounds with polyester resin is not sufficient, a prolonged mixing period is necessary in order to obtain an effective depression of melt viscosity. Such a prolonged mixing period is not favourable for obtaining a polyester resin compound with a retained high degree of polymerization, because the degree of polymerization is considerably affected by the time and temperature during the mixing.

SUMMARY OF THE INVENTION

Thus, an object of the present invention is to find a melt viscosity depressant capable of depressing the melt viscosity of a polyester resin without essentially reducing the degree of polymerization thereof. Another object of the present invention is to obtain a high molecular weight polyester resin composition with a reduced melt viscosity by adding such a melt viscosity depressant, and to obtain a high strength polyester resin molding product or fiber, especially a cationic dye-dyeable polyester fiber having a sufficient strength.

It has now been found that the addition of specific melt viscosity depressants to a polyester resin provides a polyester resin composition having a greatly depressed melt viscosity without reducing the degree of polymerization of the resin, which polyester resin composition thereby provides a high strength molding product or fiber, especially a cationic dye-dyeable fiber with a sufficient strength.

The present invention relates to a melt viscosity depressant for a polyester resin comprising an aromatic carbonyl compound represented by formula (I) or (II):

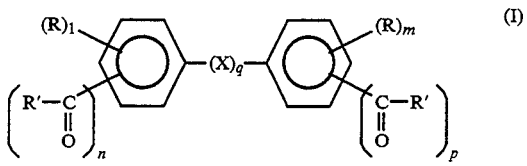

wherein R represents an alkyl group or an alkoxy group,

R' represents a hydrocarbon group, l and m each represent such an integer that l+m is 0 to 3, n and p each represent such an integer that n+p is 1 or 2, q represents 0 or 1, and X represents

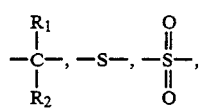

wherein $R_1$ and $R_2$ each represent a hydrogen atom or an alkyl group having 4 or less carbon atoms, and

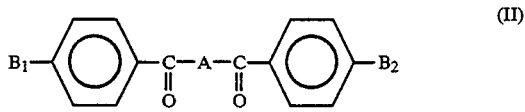

wherein $B_1$ and $B_2$ each represent an alkyl group, an alkenyl group, an acyl group or an alkoxy group having 3 to 18 carbon atoms, A represents a divalent aliphatic hydrocarbon group, a divalent alicyclic hydrocarbon group or a divalent aromatic hydrocarbon group.

The present invention relates to a polyester resin composition comprising a polyester resin and the above described melt viscosity depressant.

The present invention also relates to a polyester fiber produced by melt-spinning the above described polyester resin composition and a process for producing the same.

DETAILED DESCRIPTION OF THE INVENTION

In formula (I), R and R' represent an alkyl group or an alkoxy group, and a hydrocarbon group, respectively. The total number of carbon atoms of R and R' in a molecule is preferably selected from the range of the following equation:

$$9 \leq R \times (l+m) + R' \times (n+p) \leq 56$$

If it is less than 9, the compound of formula (I) has a too low molecular weight and is liable to evaporate at the melting temperature of the polyester resin, causing bubbles in the resin or contaminating the spinning nozzle by the fume.

If it exceeds 56, the compatibility with the resin is deteriorated and the effect of the addition thereof being insufficient or causing instability of the spinning.

The total number of carbon atoms of R and R' in a molecule is more preferably below 42.

Specific examples of R in formula (I) include straight chain alkyl groups, e.g. methyl, ethyl, n-propyl, n-butyl, n-hexyl, n-octyl, n-decyl, n-dodecyl, n-tetradecyl, n-hexadecyl, n-octadecyl, n-eicosyl or n-docosyl group; branched alkyl groups, e.g. iso-propyl, iso-butyl, sec-butyl, tert-butyl, iso-pentyl, neo-pentyl, tert-pentyl, 2-ethylhexyl, 1-hexylnonyl, 1-butylpentyl, methyl-branched-heptadecyl, 1,1,3,3-tetramethylbutyl, 1,3,5-trimethylhexyl or 1,3,5,7-tetramethyloctyl group; and alkoxy groups, e.g. n-propoxy, n-butoxy, n-hexyloxy, n-octyloxy, n-decyloxy, n-dodecyloxy or 2-ethylhexyloxy group.

Specific examples of R' in formula (I) include straight chain alkyl groups, e.g. methyl, ethyl, n-propyl, n-butyl, n-pentyl, n-hexyl, n-heptyl, n-nonyl, n-undecyl, n-tridecyl, n-pentadecyl, n-heptadecyl, n-nonadecyl or n-heneicosyl group; branched alkyl groups, e.g. 1-hexylnonyl, 1-butylpentyl or methyl-branched-heptadecyl group; alicyclic groups, e.g. cyclohexyl group; alkenyl groups, e.g. 8-heptadecenyl or 9-decenyl group; and aralkyl groups, e.g. benzyl or 2-phenylethyl group.

In formula (I) l and m represent an integer that l+m is 0 to 3, and n and p each represent such an integer that n+p is 1 or 2.

Among the compounds represented by formula (I), those compounds wherein l and m are 0 respectively and n and p are 1 respectively are the preferred ones in the present invention; namely those compounds represented by formula (III).

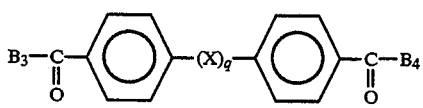 (III)

In formula (III) the carbon atom number each of $B_3$ and $B_4$ is arbitrarily selected from the range of from 5 to 21. If it is less than 5, the compound of formula (III) has a too low molecular weight and is liable to evaporate at the melting temperature of the polyester resin, causing bubbles in the resin or contaminating the spinning nozzle by the fume. If it exceeds 21, the compatibility with the polyester resin is deteriorated and the effect is not sufficient.

Specific examples of $B_3$ and $B_4$ in formula (III) include straight chain alkyl groups, e.g. n-pentyl, n-hexyl, n-heptyl, n-nonyl, n-undecyl, n-tridecyl, n-pentadecyl, n-heptadecyl, n-nonadecyl or n-heneicosyl group; branched alkyl groups, e.g. 1-hexylnonyl, 1-butylpentyl or methyl-branched-heptadecyl group; alicyclic groups, e.g. cyclohexyl group; alkenyl groups, e.g. 8-heptadecenyl or 9-decenyl group; and aralkyl groups, e.g. benzyl or 2-phenylethyl group.

Among the examples of $B_3$ and $B_4$, straight or branched alkyl groups are preferable ones.

Formula (II) represents another type of carbonyl compounds of the present invention.

In formula (II) $B_1$ and $B_2$ each represent an alkyl group, an alkenyl group, an acyl group or an alkoxy group having 3 to 18 carbon atoms, and A represents a divalent aliphatic hydrocarbon group, a divalent alicyclic hydrocarbon group or a divalent aromatic hydrocarbon group.

The total number of carbon atoms of $B_1$, $B_2$ and A in a molecule is preferably selected from the range of 6 to 40.

If it is less than 6, the compound of formula (II) has a too low molecular weight and is liable to evaporate at the melting temperature of the polyester resin, causing bubbles in the resin or contaminating the spinning nozzle by the fume.

If it exceeds 40, the compatibility with the resin is deteriorated and the effect of the addition thereof being insufficient or causing instability of the spinning.

Specific examples of $B_1$ and $B_2$ in formula (II) include straight chain alkyl groups, e.g. n-propyl, n-butyl, n-hexyl, n-octyl, n-decyl, n-dodecyl, n-tetradecyl, n-hexadecyl, n-octadecyl, n-eicosyl or n-docosyl group; branched alkyl groups, e.g. iso-propyl, iso-butyl, sec-butyl, tert-butyl, iso-pentyl, neo-pentyl, tert-pentyl, 2-ethylhexyl, 1-hexylnonyl, 1-butylpentyl, methyl-branched-heptadecyl, 1,1,3,3-tetramethylbutyl, 1,3,5-trimethylhexyl or 1,3,5,7-tetramethyloctyl group; alicyclic groups, e.g. cyclohexyl group; and alkoxy groups, e.g. n-propoxy, n-butoxy, n-hexyloxy, n-octyloxy, n-decyloxy, n-dodecyloxy or 2-ethylhexyloxy group.

In formula (II) A represents a linear or branched divalent aliphatic hydrocarbon group, an unsubstituted or substituted divalent alicyclic hydrocarbon group, or an unsubstituted or substituted divalent aromatic hydrocarbon group.

Specific examples of A in formula (II) include —$(CH_2)_2$—, —$(CH_2)_3$—, —$(CH_2)_4$—, —$(CH_2)_8$—,

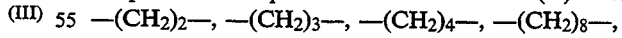

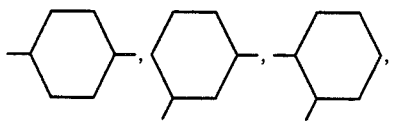

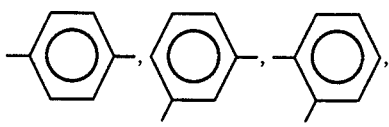

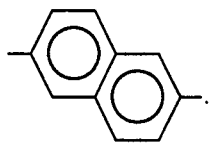

The compound of formula (I) of the present invention can easily be obtained by known methods, namely by the Friedel-Crafts reaction of a corresponding aromatic compound.

For example, the alkylation of biphenyl, diphenylether or diphenylsulfide is carried out by an alpha-olefin having from 3 to 18 carbon atoms or a halogenated alkyl compound having from 1 to 18 carbon atoms in the presence of a Lewis acid catalyst such as AlCl₃, and then the obtained product is acylated by a carboxylic acid anhydride, a carboxylic acid chloride or a carboxylic acid in the presence of a Lewis acid catalyst such as AlCl₃, resulting in the desired end product.

The compound of formula (I), wherein R represents an alkoxy group, can be obtained by acylation of a reaction product of the corresponding phenolic compound with a halogenated alkyl compound in the presence of an alkaline catalyst such as NaOH or KOH.

The compound of formula (III) of the present invention can easily be obtained by the Friedel-Crafts reaction between a corresponding aromatic compound of the formula

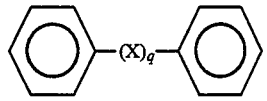

wherein X and q are the same as defined above, and a carboxylic acid, a carboxylic acid anhydride or a carboxylic acid chloride in the presence of an acid catalyst.

For example, acylation of biphenyl, diphenylether or diphenysulfide by a carboxylic acid chloride in the presence of a Lewis acid such as AlCl₃ produces the desired product.

The compound of formula (II) of the present invention can be obtained in a similar manner, namely by the Friedel-Crafts acylation of alkylbenzene or alkoxybenzene by an acid halide compound or an acid anhydride compound of the dicarboxylic acid of formula

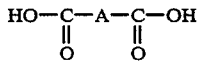

wherein A is the same as defined above.

Specific examples of the compound of formulae (I) and (II) are shown below:

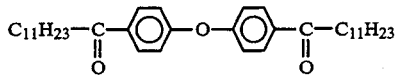
(1)

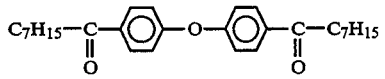
(2)

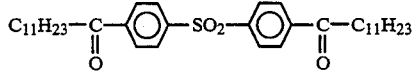
(3)

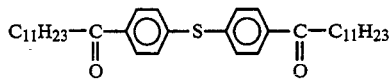
(4)

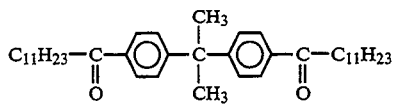
(5)

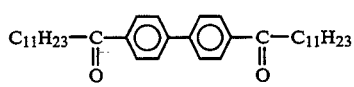
(6)

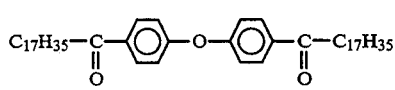
(7)

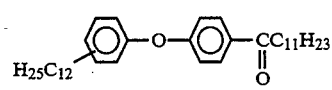
(8)

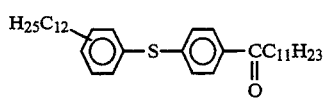
(9)

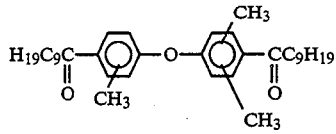
(10)

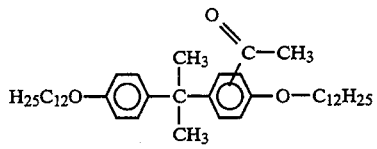
(11)

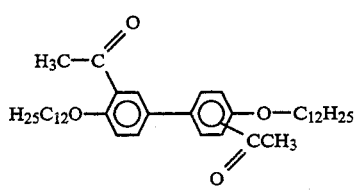
(12)

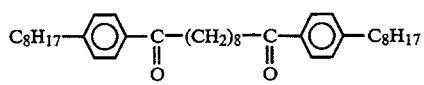
(13)

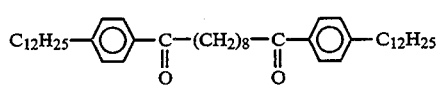
(14)

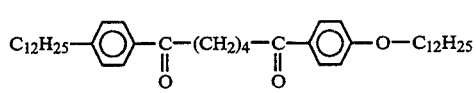
(15)

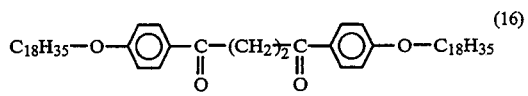
(16)

-continued

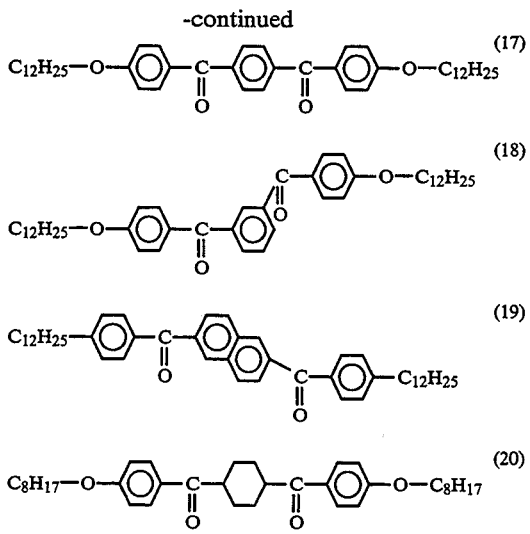

The polyester resin to be used in the present invention is a polymer obtained by copolymerising, in a conventional manner, a bifunctional carboxylic acid component comprising terephthalic acid as a main component with a glycol component comprising at least one alkylene glycol selected from ethylene glycol, trimethylene glycol and tetramethylene glycol as a main component.

Preferably, a polyester resin with the main recurring unit of ethylene terephthalate can be used. However, a part of terephthalic acid or the glycol component can be replaced by other bifunctional carboxylic acids or by other glycol compounds, respectively.

Useful bifunctional carboxylic acids other than terephthalic acid include aromatic, aliphatic or alicyclic dicarboxylic acids, e.g. isophthalic acid, naphthalenedicarboxylic acid, diphenyldicarboxylic acid, diphenoxyethanedicarboxylic acid, β-hydroxyethoxybenzoic acid, p-hydroxybenzoic acid, adipic acid, sebacic acid, and 1,4-cyclohexanedicarboxylic acid.

Useful glycol compounds other than the above mentioned alkylene glycol include aromatic, aliphatic or alicyclic diol compounds, e.g. cyclohexane-1,4-dimethanol, neopentyl glycol, bisphenol A, and bisphenol S; and polyoxyalkylene glycols.

Furthermore, a part of the terephthalic acid moiety of the polyester resin with the main recurring unit of ethylene terephthalate may be replaced by a sulfonic acid salt moiety represented by formula (IV) in order to make a cationic dye-dyeable polyester:

In formula (IV) D represents an aromatic or aliphatic group, preferably an aromatic group; $X_1$ represents an ester-forming functional group, e.g.

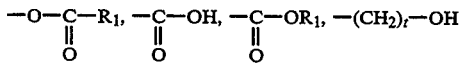

wherein $R_1$ represents a lower alkyl group or a phenyl group, and t is an integer of 1 or more; $X_2$ represents a hydrogen atom or an ester-forming functional group as defined for $X_1$, being the same as or different from $X_1$, preferably an ester-forming functional group; $M^{r+}$ represents an alkali metal cation such as sodium, potassium and lithium, an alkaline earth metal cation such as calcium and magnesium, or an onium such as tetrabutyl phosphonium, ethyltributyl phosphonium and benzyltributyl phosphonium, among which sodium is preferred; and r represents 1 or 2.

Specific examples of the compound of formula (IV) are sodium 5-sulfoisophthalic acid, sodium dimethyl 5-sulfoisophthalate, sodium di-2-hydroxyethyl 5-sulfoisophthalate, sodium di-4-hydroxybutyl 5-sulfoisophthalate, tetrabutylphosphonium 3,5-dicarboxybenzenesulfonate, ethyltributylphosphonium 3,5-dicarboxybenzenesulfonate, and benzyltributylphosphonium 3,5-dicarboxybenzenesulfonate, among which sulfoisophthalic acid salts are preferred. These sulfonates may be used either alone or as a combination of two or more thereof. A preferred copolymerization ratio of the sulfonate of formula (IV) ranges from 0.1 to 10 mol %, preferably 1 to 5 mol %, based on the total amount of the cationic dye-dyeable polyester.

The polyester resin to be used in the present invention preferably has an intrinsic viscosity [η] of 0.4 or more, and more preferably 0.5 or more, in a phenol/tetrachloroethane (60/40 by weight) solution at 25° C.

Addition of the compounds for formulae (I), (II) and/or (III) to the polyester resin system can be carried out at any stage before molding or melt-spinning the polyester resin composition.

These compounds may be added during or after the preparation of the polyester resin, and may also be added at the molding step or spinning step to the polyester resin pellets or molten resin, and then mixed.

In order to attain the desired efficiency of the melt viscosity depressants of the present invention, the compounds for formulae (I), (II) or (III) may be added in an amount of from 0.5 to 10 parts by weight, preferably from 1 to 5 parts, and more preferably from 2 to 5 parts, per 100 parts by weight of the polyester resin. If the amount is less than 0.5 parts, desired effects are hardly achieved. If the amount exceeds 10 parts, some adverse influences come out on the resin characteristics.

The melt viscosity depressants of the present invention have high heat resistance so that they do not decompose to cause fuming or colouring even when exposed to the high temperature of melt-spinning. Thus, the addition of these compounds to the polyester resin does not cause a molecular weight reduction of the polyester resin.

The melt viscosity depressants of the present invention can be used together with a known melt viscosity depressant. For example, they can be used together with the compounds disclosed in JP-A-3-223382 (1991) or JP-A-3-223383 (1991) in any proportion.

The polyester resin composition of the present invention may contain other additives which are usually used for polyester resin composition, e.g. an antioxidant, an ultraviolet ray absorbent, a flame retardant, a matting agent, a pigment, a colourant and an antistatic agent.

Using a high molecular weight polyester resin composition containing the compounds of formulae (I), (II) or (III), a high strength polyester fiber can be obtained.

For the production of a high strength polyester fiber, the melt viscosity depressant of formulae (I), (II) or (III) are uniformly mixed in the high molecular weight polyester resin, and the resulting resin composition is spun in a molten state. After cooling the spun filament is stretched and then heat-treated.

The spun filament may be wound up after cooling and then preheated with stretching followed by heat-treatment under tension on a heated roller.

It is also possible that the spun filament is taken up on a roller without being wound and subsequently stretched and heat-treated on a heated roller.

Stretching and heat-treatment can be carried out in a conventional manner employed for general polyester fibers. A preferred preheating temperature for stretching is from 60° to 100° C., and a preferred heat-treatment temperature is from 150° to 250° C.

For obtaining a high strength fiber, it is preferred that the elongation by stretching (stretching ratio) is more than four.

The melt viscosity depressants of the present invention make it possible to substantially reduce the melt viscosity of a thermoplastic polyester resin. Therefore, they facilitate mold processing and melt-spinning of a polyester resin composition having a high degree of polymerization to thereby obtain high strength polyester molding products and polyester fibers.

The present invention is now illustrated in greater detail with reference to the Examples, but it should be understood that the present invention is not deemed to be limited thereto. All percentages, parts and ratios are by weight unless otherwise indicated.

All the compounds shown by the compound number are those listed in the exemplification above.

Example 1

5 parts of each compound listed in Table 1 were added to 100 parts of polyethylene terephthalate resin and the resulting mixture was melt-kneaded in an extruder. The resulting strands were cooled with water and cut to form test samples.

The melt viscosity of the resin composition was measured with a flow tester under the following conditions: 280° C., a load of 10 kgf, a die diameter of 1.0 mm, a die length of 10 mm, and a plunger area of 1.0 cm$^2$. After the measurement of melt viscosity, the sample was then dissolved in a phenol/tetrachloroethane (60/40) solution, and the intrinsic viscosity [$\eta$] thereof at 25° C. was measured. Those samples having the same intrinsic viscosity as the control polyethylene terephthalate resin containing no additive were deemed to have undergone essentially no reduction in degree of polymerization. The results obtained are shown in Table 1.

TABLE 1

| Additive | Melt Viscosity (poise) | Intrinsic Viscosity (dl/g) |
| --- | --- | --- |
| none | 15,860 | 0.962 |
| compound (1) | 7,800 | 0.962 |
| compound (2) | 8,035 | 0.965 |
| compound (3) | 7,787 | 0.964 |
| compound (4) | 7,832 | 0.967 |
| compound (5) | 8,001 | 0.959 |
| compound (6) | 8,113 | 0.957 |

TABLE 1-continued

| Additive | Melt Viscosity (poise) | Intrinsic Viscosity (dl/g) |
| --- | --- | --- |
| compound (7) | 7,720 | 0.960 |

EXAMPLE 2

The same method as in Example 1 was carried out by using 5 parts of each compound listed in Table 2 and Table 3. The results obtained are shown in these Tables.

TABLE 2

| Additive | Melt Viscosity (poise) | Intrinsic Viscosity (dl/g) |
| --- | --- | --- |
| none | 17,350 | 0.983 |
| compound (8) | 7,984 | 0.978 |
| compound (9) | 8,237 | 0.977 |
| compound (10) | 8,295 | 0.981 |
| compound (11) | 8,312 | 0.983 |
| compound (12) | 8,351 | 0.978 |

TABLE 3

| Additive | Melt Viscosity (poise) | Intrinsic Viscosity (dl/g) |
| --- | --- | --- |
| none | 16,215 | 0.971 |
| compound (13) | 7,562 | 0.968 |
| compound (14) | 7,430 | 0.972 |
| compound (15) | 7,621 | 0.975 |
| compound (16) | 7,850 | 0.965 |
| compound (17) | 7,417 | 0.969 |
| compound (18) | 7,928 | 0.973 |
| compound (19) | 7,869 | 0.970 |
| compound (20) | 7,755 | 0.972 |

The compounds of the present invention are capable of reducing the melt viscosity of the polyester resin composition without essentially reducing the intrinsic viscosity. Therefore, they are effective in order to reduce the spinning pressure and to accelerate the spinning speed.

EXAMPLE 3

The invention compound (1) (the amount is shown in Table was added to 100 parts of a polyester resin and the resulting mixture was melt-kneaded in an extruder. The resulting strands were cooled with water and cut to form chips. The chips were placed in an extruder-type melt-spinning machine and extruded at a rate of 2.5 g/min through a spinning nozzle having a diameter of 0.5 nun while keeping the temperature of the spinning section at 300° C. The spun strand thus formed was wound up at a rate of 1,000 m/min at a position of 2.5 m beneath the nozzle. The filament thus wound up was stretched with various stretching ratios shown in Table 4 in an oil bath at 80° C. and then heat-treated at 170° C. for 30 min while keeping the filament length constant.

Table 4 shows the amount of the compound (1), intrinsic viscosity of the original polyester resin, the chip and the unstretched filament, the pressure at the nozzle, the maximum stretching ratio and the strength of the stretched filament.

TABLE 4

| Amount of compound (1) (parts) | Intrinsic Viscosity (dl/g) | | | Pressure at nozzle (kgf/cm$^2$) | Maximum stretching ratio | Strength of stretched filament (g/d) |
| --- | --- | --- | --- | --- | --- | --- |
| | Original polyester resin | Chip of composition | Unstretched filament | | | |
| 0 | 1.2 | 1.06 | 0.88 | 105 | 4 | 9.5 |

TABLE 4-continued

| Amount of compound (1) (parts) | Intrinsic Viscosity (dl/g) | | | Pressure at nozzle (kgf/cm²) | Maximum stretching ratio | Strength of stretched filament (g/d) |
|---|---|---|---|---|---|---|
| | Original polyester resin | Chip of composition | Unstretched filament | | | |
| 0 | 1.5 | 1.34 | — | 198 | — | — |
| 5 | 1.2 | 1.05 | 0.89 | 70 | 4.5 | 11.5 |
| 5 | 1.5 | 1.35 | 1.25 | 148 | 4 | 12.5 |
| 0.5 | 1.2 | 1.06 | 0.89 | 104 | 4.2 | 10.1 |
| 10 | 1.2 | 1.04 | 0.80 | 62 | 4.8 | 10.9 |

EXAMPLE 4

The same method as in Example 3 was carried out by using compound (8) or compound (13), the amount of which are shown in Tables 5 and 6, respectively. The results obtained are listed in these Tables.

TABLE 5

| Amount of compound (8) (parts) | Intrinsic Viscosity (dl/g) | | | Pressure at nozzle (kgf/cm²) | Maximum stretching ratio | Strength of stretched filament (g/d) |
|---|---|---|---|---|---|---|
| | Original polyester resin | Chip of composition | Unstretched filament | | | |
| 0 | 1.210 | 1.094 | 0.971 | 141 | 3.9 | 9.5 |
| 0.5 | 1.210 | 1.094 | 0.970 | 133 | 4.0 | 9.6 |
| 5 | 1.210 | 1.091 | 0.968 | 100 | 4.2 | 10.5 |
| 10 | 1.210 | 1.089 | 0.966 | 80 | 4.5 | 9.5 |
| 0 | 1.495 | 1.382 | — | 209 | — | — |
| 5.0 | 1.495 | 1.381 | 1.265 | 133 | 4.0 | 12.7 |

TABLE 6

| Amount of compound (13) (parts) | Intrinsic Viscosity (dl/g) | | | Pressure at nozzle (kgf/cm²) | Maximum stretching ratio | Strength of stretched filament (g/d) |
|---|---|---|---|---|---|---|
| | Original polyester resin | Chip of composition | Unstretched filament | | | |
| 0 | 1.2 | 1.04 | 0.88 | 105 | 4 | 9.5 |
| 0.5 | 1.2 | 1.05 | 0.89 | 100 | 4.2 | 10.1 |
| 5 | 1.2 | 1.05 | 0.89 | 68 | 4.6 | 11.6 |
| 10 | 1.2 | 1.04 | 0.87 | 55 | 5.1 | 10.9 |
| 0 | 1.5 | 1.33 | — | 198 | — | — |
| 5 | 1.5 | 1.34 | 1.25 | 148 | 4.1 | 12.8 |

In the Tables "-" shows a case where no filament was obtained because of breakage owing to the poor spinnability.

EXAMPLE 5

5 parts of each compound listed in Table 7 were added to 100 parts of cationic dye-dyeable polyethylene terephthalate containing 2.5 mol % of sodium 5-sulfoisophthalic acid and having an intrinsic viscosity of 0.68, and the resulting mixture was melt-kneaded in an extruder. The resulting strands were cooled with water and cut to form test samples.

The melt viscosity of the resin composition was measured with a flow tester under the following conditions: 260° C., a load of 10 kgf, a die diameter of 1.0 mm, a die length of 10 mm, and a plunger area of 1.0 cm² After the measurement of melt viscosity, the sample was then dissolved in phenol/tetrachloroethane (60/40) solution, and the intrinsic viscosity [η] thereof at 25° C. was measured. Those samples having the same intrinsic viscosity as the control polyethylene terephthalate resin containing no additive were deemed to have undergone essentially no reduction in degree of polymerization. The results obtained are shown in Table 7.

TABLE 7

| Additive | Melt Viscosity (poise) | Intrinsic Viscosity (dl/g) |
|---|---|---|
| none | 4,389 | 0.529 |
| compound (1) | 2,274 | 0.530 |
| compound (2) | 2,320 | 0.533 |
| compound (3) | 2,263 | 0.531 |
| compound (4) | 2,259 | 0.531 |
| compound (5) | 2,298 | 0.527 |
| compound (6) | 2,304 | 0.526 |
| compound (7) | 2,254 | 0.527 |

EXAMPLE 6

The same method as in Example 5 was carried out by using each compound listed in Tables 8 and 9. The results obtained are also shown in these Tables.

TABLE 8

| Additive | Melt Viscosity (poise) | Intrinsic Viscosity (dl/g) |
|---|---|---|
| none | 4,509 | 0.541 |
| compound (8) | 2,275 | 0.540 |
| compound (9) | 2,436 | 0.537 |
| compound (10) | 2,580 | 0.542 |
| compound (11) | 2,599 | 0.540 |
| compound (12) | 2,530 | 0.537 |

TABLE 9

| Additive | Melt Viscosity (poise) | Intrinsic Viscosity (dl/g) |
|---|---|---|
| none | 4,423 | 0.533 |
| compound (13) | 2,238 | 0.531 |
| compound (14) | 2,209 | 0.528 |

TABLE 9-continued

| Additive | Melt Viscosity (poise) | Intrinsic Viscosity (dl/g) |
| --- | --- | --- |
| compound (15) | 2,362 | 0.535 |
| compound (16) | 2,370 | 0.540 |
| compound (17) | 2,179 | 0.525 |
| compound (18) | 2,355 | 0.533 |
| compound (19) | 2,259 | 0.529 |
| compound (20) | 2,193 | 0.530 |

EXAMPLE 7

5 parts of compound (4) were mixed as a melt viscosity depressant with 100 parts of cationic dye-dyeable polyethylene terephthalate containing 2.5 mol % of sodium 5-sulfoisophthalic acid and having an intrinsic viscosity of 0.68.

The mixture was put in an extruder type melt-spinning machine and extruded through a spinning nozzle having a diameter of 0.5 mm at 280° C. at a spinning rate of 3 g/min. The spun strand was wound at a position 2.5 m below the nozzle at a rate of 1,000 m/min. The wound unstretched filament was stretched and heat-treated, by means of a feed roller set at 80° C. and a plate heater set at 180° C. at a stretching ratio such that the resulting stretched yarn had an elongation of 30 %.

The spinning pressure at the nozzle was 122 kgf/cm$^2$, the unstretched filament was found to have an intrinsic viscosity of 0.58, and the stretched yarn had a strength of 5.1 g/d.

EXAMPLE 8

5 parts of compound (9) or compound (16) were mixed with 100 parts of cationic dye-dyeable polyethylene terephthalate containing 2.5 mol % of sodium 5-sulfoisophthalic acid and having an intrinsic viscosity of 0.70.

The mixtures obtained were extruded, wound up, stretched and heat-treated in the same manner as in Example 7, except that the spinning rate was 3.5 g/min.

The results are shown in Table 10.

TABLE 10

| Melt Viscosity Depressant | Compound (9) | Compound (16) |
| --- | --- | --- |
| Spinning pressure at nozzle (kgf/cm$^2$) | 115 | 118 |
| Intrinsic viscosity of unstretched filament (dl/g) | 0.58 | 0.58 |
| Strength of stretched yarn (g/d) | 5.5 | 5.5 |

COMPARATIVE EXAMPLE 1

The same procedure as in Example 7 was carried out by using a cationic dye-dyeable polyethylene terephthalate containing 2.5 mol % of sodium 5-sulfoisophthalatic acid and having an intrinsic viscosity of 0.55 without adding a melt viscosity depressant. As a result, the spinning pressure at the nozzle was 127 kgf/cm$^2$, the unstretched filament had an intrinsic viscosity of 0.51, and the stretched filament had a strength of 4.0 g/d.

COMPARATIVE EXAMPLE 2

Polyester fiber was produced in the same manner as in Example 7, except for using no melt viscosity depressant. As a result, the pressure at the spinning nozzle reached 172 kgf/cm$^2$, and breaking occurred due to poor spinnability.

What is claimed is:

1. A polyester resin composition comprising a polyester resin, and
a melt viscosity depressant for a polyester resin wherein said melt viscosity depressant comprises:
an aromatic carbonyl compound represented by formula (I) or (II):

(I)

wherein
R represents an alkyl group or an alkoxy group,
R' represents a hydrocarbon group,
wherein the total number of carbon atoms of R and R' in a molecule is selected from the range determined by the following equation:

$$9 \leq R \times (l+m) + R' \times (n+p) \leq 56,$$

l and m each represent such an integer than l+m is 0 to 3,
n and p each represent such an integer that n+p is 1 or 2,
X represents wherein
R$_1$ and R$_2$ each represent a hydrogen atom or an alkyl group having 4 or less carbon atoms, and (II)

wherein B$_1$ and B$_2$ each represent an alkyl group, an alkenyl group, an acyl group or an alkoxy group having 3 to 18 carbon atoms,
A represents a divalent aliphatic hydrocarbon group, a divalent alicyclic hydrocarbon group or a divalent aromatic hydrocarbon group.

2. The polyester resin composition of claim 1, wherein said melt viscosity depressant for a polyester resin is represented by formula (III):

(III)

wherein
B$_3$ and B$_4$ each represent a hydrocarbon group having 5 to 21 carbon atoms, and l and X are as defined in claim 1.

3. The polyester resin composition of claim 2, wherein B$_3$ and B$_4$ each represent an alkyl group having 5 to 21 carbon atoms.

4. The polyester resin composition of claims 1, 2, or 3 wherein the polyester resin is a polyester resin with the main recurring unit of ethylene terephthalate.

5. The polyester resin composition of claims 1, 2, or 3 wherein the polyester resin is a polyester resin with the main recurring unit of ethylene terephthalate and a part of the terephthalaic acid moiety is replaced by a sulfonic acid salt moiety represented by formula (IV).

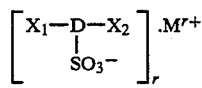
(IV)

wherein D represents an aromatic or aliphatic group;

X$_1$ represents an ester-forming functional group; X$_2$ represents a hydrogen atom or an ester-forming functional group which may be the same as or different from X$_1$; M$^{r+}$ represents an alkali metal cation, an alkaline earth metal cation, or an onium; and r represents 1 or 2.

6. The polyester resin composition according to claims 1, 2, or 3, wherein the amount of the melt viscosity depressant for a polyester resin is 0.5 to 10 parts by weight per 100 parts by weight of said polyester resin.

7. A polyester fiber produced by melt-spinning the polyester resin composition according to claims 1, 2, or 3.

8. A process for producing a polyester fiber comprising melt-spinning the polyester resin composition according to claims 1, 2, or 3.

9. The polyester resin composition of claim 1, wherein said melt viscosity depressant for a polyester resin is represented by formula (I), wherein n+p=1.

10. The polyester resin composition of claim 1, wherein said melt viscosity depressant for a polyester resin is represented by formula (I), wherein X represents

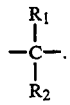

11. The polyester resin composition of claim 1, wherein said melt viscosity depressant for a polyester resin is selected from the group consisting of

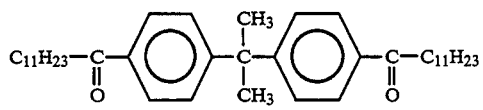

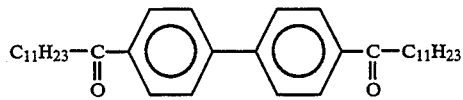

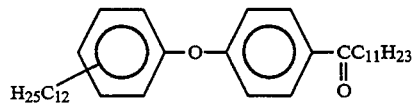

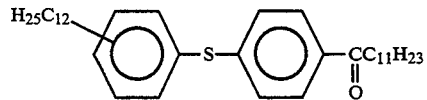

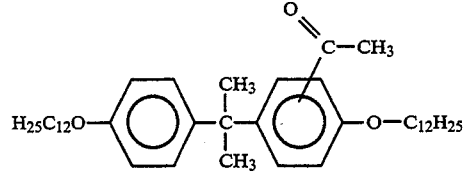

and

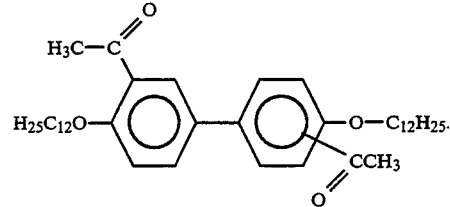

* * * * *

UNITED STATES PATENT AND TRADEMARK OFFICE
CERTIFICATE OF CORRECTION

PATENT NO. : 5,340,521
DATED : August 23, 1994
INVENTOR(S) : Akito Itoi, et al

It is certified that error appears in the above-indentified patent and that said Letters Patent is hereby corrected as shown below:

Column 14, lines 29 and 30 insert --q represents 0 or 1, and--

Signed and Sealed this

Twentieth Day of December, 1994

Attest:

BRUCE LEHMAN

*Attesting Officer*  *Commissioner of Patents and Trademarks*